Figure 1:
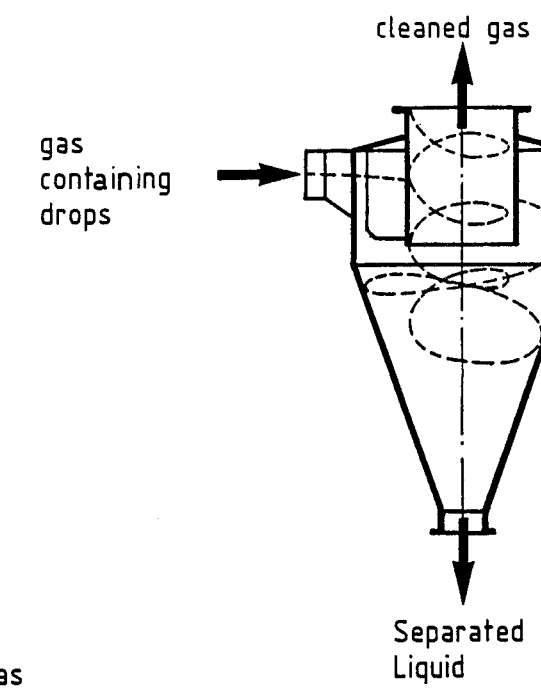
Figure 2:
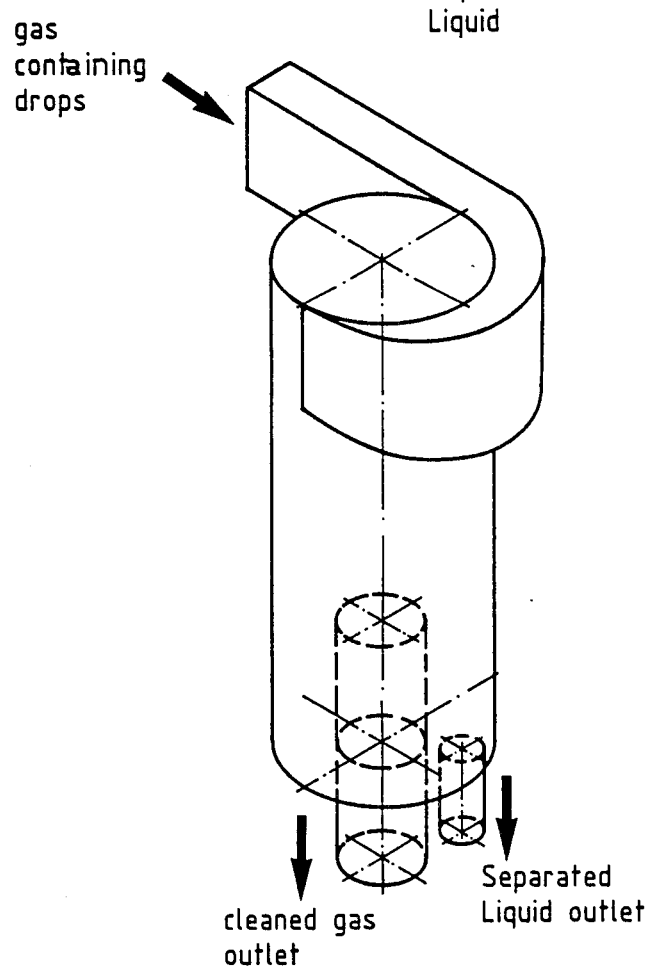

United States Patent [19]

Borho et al.

[11] Patent Number: 4,616,094

[45] Date of Patent: Oct. 7, 1986

[54] ISOLATION OF LIQUID UREA FROM THE OFF-GAS OF THE SYNTHESIS OF MELAMINE

[75] Inventors: Klaus Borho, Mutterstadt; Dieter Fromm, Gruenstadt; Ernst-Juergen Schier, Altleiningen; Hans H. Schneehage, Weisenheim; Alfred Widmann, Mutterstadt, all of Fed. Rep. of Germany

[73] Assignee: BASF Aktiengesellschaft, Ludwigshafen, Fed. Rep. of Germany

[21] Appl. No.: 568,500

[22] Filed: Jan. 5, 1984

Related U.S. Application Data

[63] Continuation of Ser. No. 287,785, Jul. 28, 1981, abandoned.

[30] Foreign Application Priority Data

Aug. 18, 1980 [DE] Fed. Rep. of Germany ....... 3031124

[51] Int. Cl.$^4$ ............................................. C07C 126/08
[52] U.S. Cl. ..................................... 564/073; 564/67; 544/203
[58] Field of Search ..................... 564/73, 67; 544/203

[56] References Cited

U.S. PATENT DOCUMENTS 3,979,392  9/1976  Eguchi et al. ................... 564/73 X Primary Examiner—Robert V. Hines
Attorney, Agent, or Firm—Keil & Weinkauf

[57] ABSTRACT

A process for isolating liquid urea and its thermal decomposition products from the off-gas of melamine synthesis, which gas has been freed from melamine by fractional condensation and then been washed with molten urea, wherein the off-gas, containing 2–10 kg of melt per kg of pure gas, is passed at 8–30 m/sec tangentially into the upper part of an axially symmetrical separation zone. As a result of the rotation imparted to the gas/liquid mixture, the two phases are separated from one another, and both pass downward through the separation zone. The gas and liquid are separately taken off at the bottom end of the separation zone. The residence time of the gas mixture in the separation zone is not less than 0.5 second.

3 Claims, 1 Drawing Figure

ISOLATION OF LIQUID UREA FROM THE OFF-GAS OF THE SYNTHESIS OF MELAMINE

This is a continuation of application Ser. No. 287,785, filed July 28, 1981, now abandoned.

The present invention relates to a process for the isolation of liquid urea or a mixture of liquid urea and its thermal decomposition products from the off-gas mixture arising in the synthesis of melamine.

To synthesize melamine, urea and/or its thermal decomposition products are heated at 350°–400° C. in the presence of a catalyst and of added ammonia. To work up the synthesis gas, containing melamine vapor, the gas is subjected to fractional condensation, ie. it is cooled to 170°–250° C., at which temperature the melamine crystallizes out selectively and almost completely from the gas stream, and is separated off. The gas mixture which remains after isolating the melamine, and which essentially consists of ammonia and carbon dioxide, however still contains melamine, in an amount depending on its vapor pressure, and urea which has been left unconverted in the synthesis, in the form of its thermal decomposition product isocyanic acid.

German Pat. No. 1,204,679 discloses a method for cooling the gases further and isolating these impurities, wherein the gas is washed with a melt of urea or of a mixture of urea and its thermal decomposition products. On washing with molten urea, the gas stream necessarily entrains small droplets of urea which must be separated out in downstream droplet separators, for example packed columns, lamellar separators or cyclones. The deposition surfaces of such apparatus become encrusted, on sustained operation, with urea decomposition products which are insoluble in the urea melt, for example with cyanuric acid, melamine cyanurate and the like.

Such encrusting occurs particularly on apparatus surfaces on which the liquid urea is exposed to an elevated temperature for a lengthy period. In an extreme case, a droplet adhering to a deposition surface may be converted completely to its decomposition products.

Further, it is known from German Pat. No. 1,670,216 that such crusts can be removed by periodically flooding the droplet separator with urea melt. To ensure continuous operation, the urea washer must be followed by several of these droplet separators, which are alternately in operation or in process of being cleaned by flooding with urea melt.

German Published Application DAS No. 2,440,315 proposes circumventing this disadvantage by passing the gases, which contain the entrained liquid droplets, through a separator (cyclone separator, impingement separator with deflector plates or lamellar separator) in order to separate out the liquid droplets by collision with the inner surface of the separator, these surfaces being provided with a downward-flowing film of molten urea, of a molten mixture of urea and its thermal decomposition products and/or a molten mixture thereof with melamine. Even though the period for which a separator can be operated is increased by this measure, the production of a continuous liquid film entails considerable expenditure on apparatus, as well as technical effort, and furthermore, even with these measures, satisfactory operating periods cannot be achieved.

It is true that in lamellar separators a coherent liquid film can be produced by spraying liquid onto the deposition surfaces which face the gas inlet, and this film prevents encrusting of the surfaces; however, to maintain the efficiency of the separator it is absolutely essential that the separation surfaces on the gas exit side should be exposed to as little liquid as possible. Accordingly, progressively growing crusts develop on these rear separation surfaces; these interfere with the separation function of the surfaces, accordingly also lead to crust formation in the downstream lines, and therefore make it necessary to shut down, and clean, the apparatus at regular intervals, in spite of the fact that the separator has been provided with a film of melt.

Cyclone separators, which are also mentioned in the cited DAS, give even less satisfactory results in respect of separating out droplets of urea melt. As is known from the literature (cf. Chemie-Ingenieur-Technik 25, (1953), 328–330), special measures must be taken, when separating out liquids from gases in cyclones, in order to prevent entrainment of liquid by the gas leaving the separator. This entrainment is due to the fact that under the influence of the pressure difference existing between the center and the periphery of the tubulent zone, the liquid projected onto the outer wall of the cyclone creeps along the cyclone lid to the dip tube located in the center of the lid and serving as a gas outlet, runs downward along this tube and is there seized and entrained by the upward-flowing stream of gas.

With normal liquids, this creeping can be reduced by concentric rings arranged around the outlet tube. To separate out the small amount of liquid which creeps even past these inner barriers, the publication cited above recommends taking additional design measures, downstream of the gas outlet tube, to deflect this liquid creeping along the inner wall of the dip tube.

When separating out droplets of urea melt from the off-gases of melamine synthesis, such measures cannot be applied, since it is specifically the urea accumulating at the stated positions which preferentially undergoes thermal decomposition and leads to encrusting. Neither can these difficulties be overcome by additionally providing the walls of the cyclone with a downward-flowing film of molten urea.

It is an object of the present invention to provide a process for isolating liquid urea or a mixture of liquid urea and its thermal decomposition products from the off-gases of the synthesis of melamine, which arise on catalytic conversion of urea at an elevated temperature, and have been freed from melamine by fractional condensation and subsequently been washed with molten urea or a mixture of molten urea and its thermal decomposition products, which can be carried out without major expenditure on apparatus and major technical effort, ensures effective separation of the gas from the liquid phase and also avoids encrusting of the separation system and of the lines downstream thereof.

We have found that this object is achieved if the gas-liquid mixture coming from the wash zone and containing 2–10 kg of the melt per kg of pure gas is passed tangentially, at a velocity of 8–30 m/sec, into the upper part of an axially symmetrical separation zone, where, due to the rotation imparted to the gas-liquid mixture, the two phases are separated from one another and both are moved downward, in the same direction, through the separation zone, and gas and separated-out liquid are taken off separately from one another at the bottom end of the separation zone, the mean residence time of the gas mixture in the separation zone being not less than 0.5 second.

Usually, the gas freed from melamine is washed with 5–10 kg of urea melt, or of a mixture of molten urea and its thermal decomposition products, per kg of gas. Accordingly, in the process according to the invention, in contrast to the conventional processes, not only the melt droplets entrained by the gas, but, particularly advantageously, all or at least a substantial part of the wash liquid, are introduced, together with the gas, into the separation zone.

Surprisingly, it proves possible, in the process according to the invention, to prevent the walls of the separation zone and of the downstream lines from becoming encrusted by thermal decomposition products of urea, such as cyanuric acid or melamine cyanurate, and hence to prevent a reduction in separating efficiency, without providing the separator surfaces with a downward-flowing film of liquid and without cleaning the separation zone by periodically flooding it with a melt of urea or of a mixture of urea and its thermal decomposition products.

A further characteristic of the process according to the invention is that the gas and the liquid separated out by the centrifugal forces are passed in the same direction through the separation zone, thereby reducing the residence time of the melt and accordingly reducing the formation of decomposition products.

Furthermore, it is important that the velocity limits stated above be maintained at the inlet of the separation zone. Adequate separation is only ensured at velocities $\geq 8$ m/s, whilst on the other hand velocities of 30 m/s should not be exceeded, since, if they are, liquid droplets deposited on the wall become detached again and are entrained by the gas stream leaving the separation zone, leading to encrusting and ultimately to blockage of the lines and apparatus units downstream of the separation system.

Maintaining a minimum residence time of 0.5 second is of considerable importance if the droplets present in the gas are to be separated out completely. Whilst theoretically the separation efficiency progressively improves with increasing residence time, the latter should not exceed 5 seconds for practical reasons, and in order to avoid decomposition in the melt.

The process according to the invention is illustrated below in relation to the diagrammatic FIGURE:

The off-gas which has been freed from melamine and still contains unconverted urea, as well as melamine in an amount proportional to its vapor pressure, passes through the line (1) into the washer (2). Wash liquid, for example a urea melt, is introduced through line (3). At the bottom end of the washer, the gas and melt are taken off conjointly and are introduced tangentially, through the inlet (4), into the axially symmetrical, preferably cylindrical, separator (5).

As a result of the rotation imparted to it, the melt is projected against the wall and moves spirally downward along the latter. The gases, which also move downward, leave the separation zone through the dip tube (6) which protrudes into the bottom of the separation zone, whilst the liquid collects on the bottom and is taken off through the tube (7). In the lower part of the separator, starting at the upper end of the dip tube and extending to the bottom of the separation zone, a calming area develops, thereby reliably preventing entrainment of liquid by the gas stream. Furthermore, it is not possible for creeping films of liquid to reach the upper orifice of the dip tube, since they would have to overcome gravity to do so. As a result of there being a sharp transition, in this area, between liquid and dry wall of the dip tube, encrusting cannot occur. Experiments on a transparent model apparatus operated with a mixture of air and water having reduced surface tension, have shown that if the measures prescribed according to the invention are observed, spiral strands of liquid which migrate downward along the wall and which randomly change their position are formed. Surprisingly, this phenomenon efficiently prevents encrusting when the apparatus is operated with an off-gas containing urea melt.

The Examples which follow illustrate the advantages of the process according to the invention.

EXAMPLE (A) 19,000 kg/h of a gas which has already been substantially freed from melamine are washed with 130,000 kg/h of a urea melt, which contains melamine and thermal decomposition products of urea, and are then introduced, at a velocity of 14 m/s, tangentially into a cyclone of conventional construction, having a length:diameter ratio of 3:1. The gas separated off escapes upward through a dip tube and the urea melt which has been separated out is taken off downward. After as little as 14 days, 20 kg/hour of urea melt which has not been separated out in the cyclone can be taken off a gravity separator downstream of the cyclone. After 20 days, this amount has risen to 40 kg/h. The separation efficiency of the cyclone cannot be improved by varying the gas throughput rate.

After as little as 14 days, substantial deposits of urea decomposition products are found in the dip tube and in the downstream gas lines.

(B) The gas-liquid mixture described in (A) and coming from the urea wash of a melamine production unit is passed, at a velocity of 24 m/s, tangentially into a cylindrical separation zone and flows downward through the latter at an axial velocity of 4 m/s. After a residence time of 2 seconds, the gas mixture which has been freed from urea leaves the separation zone, at the bottom end, through a central tube. The urea melt separated off is also taken off at the bottom. Even after 8 months' operation, no liquid urea is found in the gravity separator downstream of the separation zone. During this period, there is also no troublesome deposition of urea decomposition products on the walls of the gas outlet tube, or in the downstream lines. The separation efficiency of the separation zone remains constant even though, in production operation, the amount of gas fluctuates between 14,000 and 22,000 kg/h.

We claim:

1. In a process for isolating liquid urea or a mixture of liquid urea and its thermal decomposition products from the off-gases of the synthesis of melamine, which arise on catalytic conversion of urea at an elevated temperature, and have been freed from melamine by fractional condensation and subsequently been washed with a wash liquid comprising molten urea or a mixture of molten urea and its thermal decomposition products, the improvement which comprises: passing the gas-liquid mixture coming from the wash zone and containing 2–10 kg of the melt per kg of pure gas tangentially, at a velocity of 8–30 m/sec, into the upper part of an axially symmetrical separation zone, where, due to the rotation imparted to the gas-liquid mixture, the two phases are separated from one another and both are moved downward, in the same direction, through the separation zone, and gas and separated-out liquid are taken off separately from one another at the bottom end of the separation zone, the mean residence time of the gas mixture in the separation zone being not less than 0.5 second.

2. The process of claim 1 wherein at least a substantial portion of the wash liquid is passed from the wash zone into the separation zone.

3. The process of claim 1 wherein all of the wash liquid is passed from the wash zone into the separation zone.

* * * * *